United States Patent [19]

Zhou

[11] Patent Number: 5,702,441
[45] Date of Patent: Dec. 30, 1997

[54] METHOD FOR RAPID IMPLANTATION OF SHAPE TRANSFORMABLE OPTICAL LENSES

[75] Inventor: Stephen Q. Zhou, Hacienda Heights, Calif.

[73] Assignee: Kabi Pharmacia Ophthalmics, Inc., Monrovia, Calif.

[21] Appl. No.: 607,417

[22] Filed: Feb. 28, 1996

Related U.S. Application Data

[63] Continuation of Ser. No. 194,079, Feb. 9, 1994, abandoned.

[51] Int. Cl.⁶ .................................................. A61F 2/16
[52] U.S. Cl. ...................................... 623/6; 606/107
[58] Field of Search .............................. 623/6; 606/107

[56] References Cited

U.S. PATENT DOCUMENTS

| | | | |
|---|---|---|---|
| 4,214,585 | 7/1980 | Bailey, Jr. ............... | 128/303 R |
| 4,369,284 | 1/1983 | Chen ......................... | 524/476 |
| 4,573,998 | 3/1986 | Mazzocco .................. | 623/6 |
| 4,618,213 | 10/1986 | Chen ......................... | 350/96.34 |
| 4,681,102 | 7/1987 | Bartell ....................... | 128/303 R |
| 4,702,244 | 10/1987 | Mazzocco .................. | 128/303 R |
| 4,747,404 | 5/1988 | Jampel et al. .............. | 128/303 R |
| 4,763,650 | 8/1988 | Hauser ....................... | 128/303 R |
| 4,765,329 | 8/1988 | Cumming et al. .......... | 128/303 R |
| 4,813,954 | 3/1989 | Siepser ....................... | 623/6 |
| 4,833,890 | 5/1989 | Kelman ...................... | 623/6 |
| 4,834,094 | 5/1989 | Patton et al. ............... | 128/303 R |
| 4,834,750 | 5/1989 | Gupta ......................... | 623/6 |
| 4,836,201 | 6/1989 | Patton et al. ............... | 128/303 R |
| 4,852,566 | 8/1989 | Callahan et al. ........... | 128/303 R |
| 4,862,885 | 9/1989 | Cumming .................. | 128/303 R |
| 4,919,130 | 4/1990 | Stoy et al. .................. | 128/303 R |
| 4,934,363 | 6/1990 | Smith et al. ................ | 128/303 R |
| 4,936,850 | 6/1990 | Barrett ....................... | 623/6 |
| 4,957,505 | 9/1990 | McDonald .................. | 623/6 |
| 4,993,936 | 2/1991 | Siepser ....................... | 425/408 |
| 5,066,297 | 11/1991 | Cumming .................. | 606/107 |
| 5,098,439 | 3/1992 | Hill et al. ................... | 606/107 |
| 5,100,410 | 3/1992 | Dulebohn .................. | 606/107 |
| 5,123,905 | 6/1992 | Kelman ...................... | 606/107 |
| 5,190,552 | 3/1993 | Kelman ...................... | 606/107 |
| 5,190,553 | 3/1993 | Kanert et al. ............... | 606/107 |
| 5,201,763 | 4/1993 | Brady et al. ................ | 623/6 |
| 5,269,813 | 12/1993 | Yoshida et al. ............ | 623/6 |
| 5,275,604 | 1/1994 | Rheinish et al. ........... | 606/107 |
| 5,444,106 | 8/1995 | Zhou et al. ................. | 523/107 |

OTHER PUBLICATIONS

Samuel Masket, M.D., "Consultation Section," *Cataract Refract Surg*, vol. 18, Mar. 1992, pp. 206–214.

*Primary Examiner*—Mary Beth Jones

[57] ABSTRACT

A shape transformable medical implant or optical lens capable of substantial recoverable deformation in all dimensions is rapidly inserted and positioned into a target site such as an eye through an ejector having a small diameter, elongate, generally tubular outlet. The medical implant or optical lens is formed of a material having an elongation at break greater than 100% facilitating its ejection into the eye through a tubular outlet having an inner diameter of 3 mm or less. The ejector is provided with a precisely pressurizable chamber for the controlled displacement of the medical implant or optical lens through the small diameter, elongate, generally tubular outlet.

26 Claims, 4 Drawing Sheets

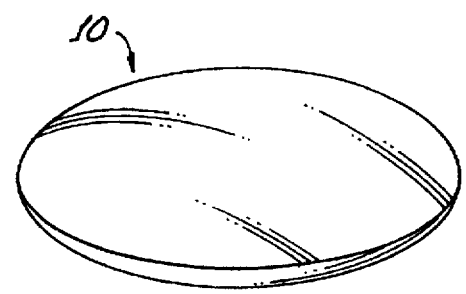
FIG. 1.
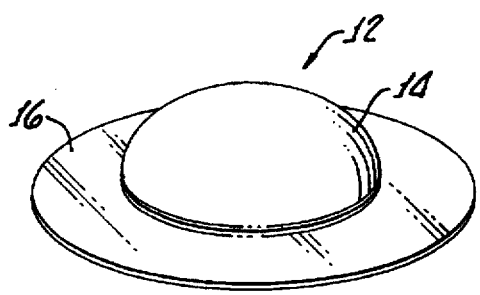
FIG. 2.
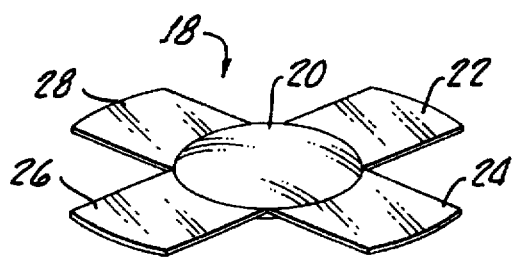
FIG. 3.
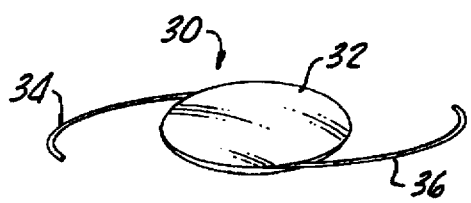
FIG. 4.
  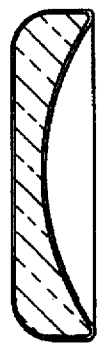 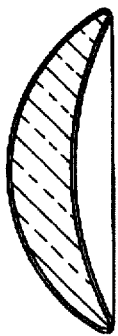
FIG. 5a.   FIG. 5b.   FIG. 5c.   FIG. 5d.

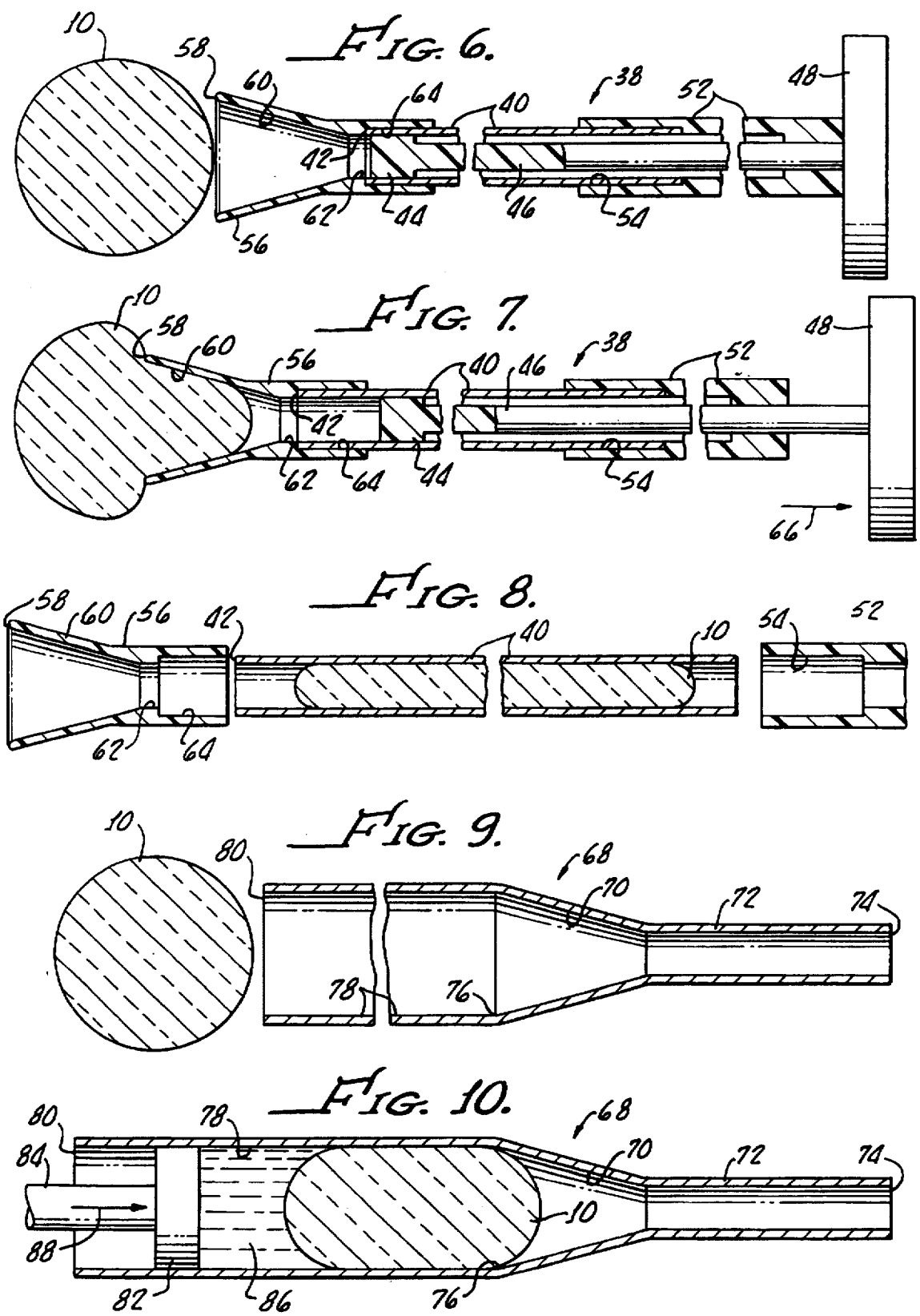

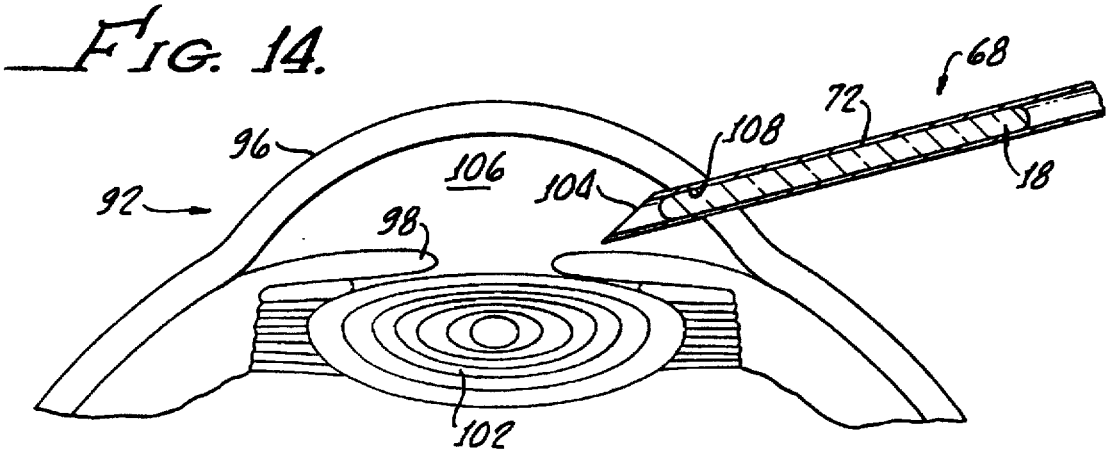
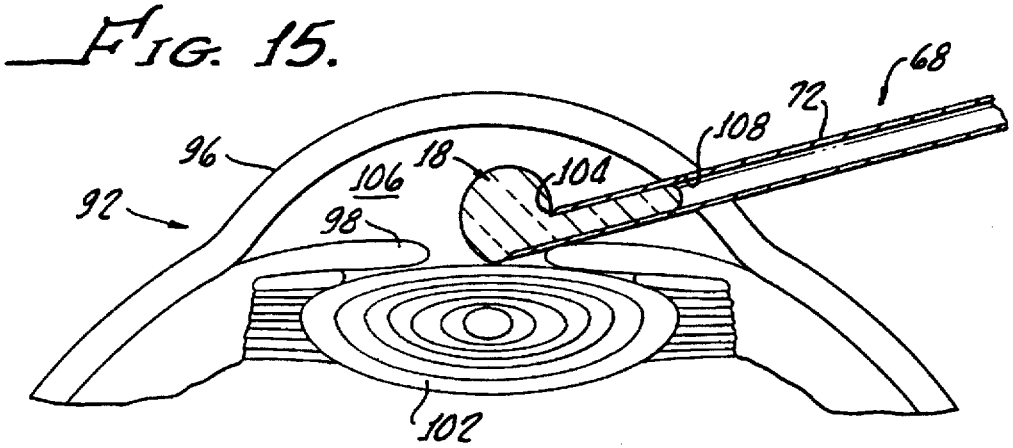
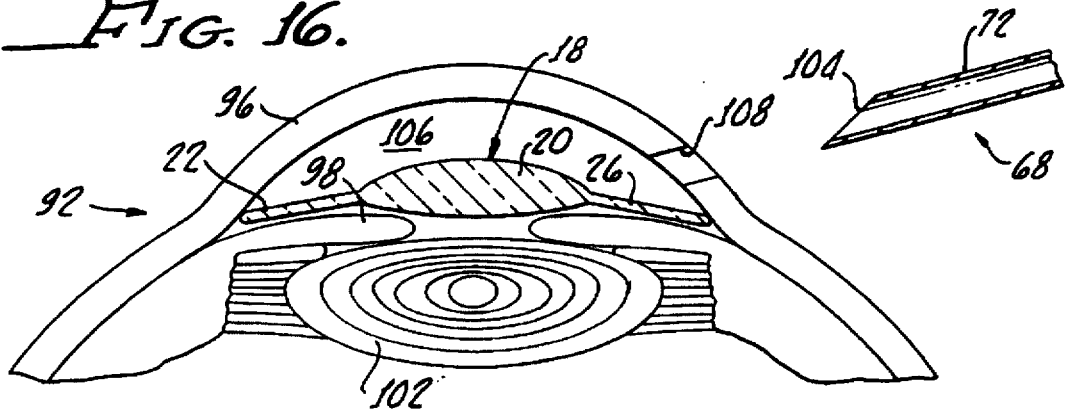

METHOD FOR RAPID IMPLANTATION OF SHAPE TRANSFORMABLE OPTICAL LENSES

This is a divisional application of U.S. patent application Ser. No. 08/194,079 filed on Feb. 9, 1994, now abandoned.

FIELD OF THE INVENTION

The present invention generally relates to methods and associated apparatus for the insertion and placement of medical implants, particularly intraocular lenses. More particularly, the present invention is directed to methods for the surgical implantation of rapidly shape transformable implants, through an ejector apparatus having a very small diameter, elongate, tubular outlet suitable for very small incision implantation techniques. The elastomeric or gelatinous, highly extensible implants possess lasting memories enabling them to recover their original conformational shapes immediately upon passage through the ejection apparatus allowing for their rapid implantation and positioning.

BACKGROUND OF THE INVENTION

The replacement or augmentation of natural body parts with medical implants is a mature technology having a wide variety of well-developed applications and techniques. Many surgically implanted medical devices perform useful and often essential functions based upon a variety of mechanical properties, including strength and flexibility. Common examples of such widely known medical implants include replacement heart valves and artificial joints. However, another class of medical implants performs useful and desirable functions by virtue of the physical shape of the implant rather than its structural or mechanical properties. Representative examples of this class of medical implants include cosmetic devices designed to augment or replace missing tissue or, more importantly, artificial optical lenses designed to replace or augment the natural lens of the eye. With respect to optical implants, it is the shape of the lens itself that, in conjunction with the refractive index of the lens material, provides the useful light-focussing function. Other minor structural features may be present to assist in the placement or retention of these devices following implantation.

Recent trends in implantation surgery have been directed toward the reduction of patient trauma, discomfort, healing time, and the associated complications that may occur through the utilization of reduced size or small incision surgical implantation techniques. The relatively rapid development of arthroscopic and microsurgery techniques and instruments has greatly facilitated the ability of the implanting surgeon to confine the physical impact of the surgical procedure to the desired target location which is accessed through a small, often remote incision. In this manner, the implanting surgeon is able to avoid trauma and damage to intervening tissues that would normally be cut and moved aside to provide surgical access using conventional large incision surgical techniques.

Unfortunately, the development of small incision techniques has not been particularly successful in conjunction with the implantation of medical devices. The principal impediments to the development of small incision techniques for use in conjunction with medical implants are the volume, the size and rigidity of the implants themselves. For example, the typical intraocular lens implant includes an optical lens portion having a minimum diameter on the order of 6 mm. Current trends in the posterior chamber implantation of intraocular lens utilize what are known as "full-sized" optics having lens diameters of 9 mm or more. As a result, the intraocular lens implantation procedure must utilize a surgical incision at least as large as the minimum dimension of the optical implant.

This is a particularly frustrating circumstance for many ocular surgeons in that the current procedures for removal of damaged or cataractous lenses require surgical incisions of only 3 to 4 mm. Thus, the implanting surgeon is required to enlarge a relatively small opening in order to implant the intraocular lens. In the ocular environment, these lengthened incisions have the additional drawback of possibly inducing postoperative astigmatism or corneal distortions in addition to the risks of increased complications and healing time.

Contemporary efforts at developing "small incision" intraocular lenses (commonly defined as capable of implantation through an incision of 4 mm in length or less) have been focussed in several different directions. For example, foldable lenses having optical portions formed of silicone have been proposed that may enable the diameter of the lens optic to be reduced by half through the folding or rolling of the lens prior to insertion. Alternatively, expansile lenses made of materials such as hydrogels may be desiccated prior to insertion to reduce the overall volume and dimensional characteristics of the lens. Following implantation, the hydrogel material hydrates and expands to its desired size. More speculative proposals include balloon lenses which may be inserted in the deflated state and then filled with a highly refractive material to form the final lens configuration. Similarly, injectable lenses have been proposed wherein a liquid polymer is injected into the naturally occurring lens capsule where the polymer cures into its final, hopefully lens shaped, form.

Though theoretically capable of small incision implantation, each of these proposals has significant drawbacks making them difficult, if not impossible, to use. While folding a silicone lens will reduce one dimension, it necessarily doubles the folded over dimension and leaves the third dimension unchanged so that the potential for small incision implantation may not be achieved. Further, folding the lenses may produce permanent deformation in the optic portion, rendering them ineffectual as an optical lens following implantation. Conversely, while it is possible to significantly reduce the dimensions of hydrogel lenses, the current state of the art requires a 3-to-24 hour hydration period following implantation. At present, this is unacceptable to the implanting surgeon who is unable to determine if the lens is properly positioned prior to complete hydration. As a result, implanting surgeons are reluctant to close the implantation incision until they are certain that access to the interior of the eye is no longer necessary. Balloon lenses have their own problems in that it is difficult to inflate the balloon with any degree of accuracy or control following implantation. Thus, the actual refractive characteristics of the lens is difficult to control. Moreover, complete removal of air bubbles from the balloon remains a significant problem. Similarly, injectable lenses cannot produce predictable optical power and resolution because the natural capsular bag will not consistently produce the necessary or desired lens shape.

Accordingly, one of the primary objects of the present invention is to provide a method for the rapid implantation of an optical lens into an eye through a minimally traumatic surgical procedure.

It is an additional object of the present invention to provide a general implantation methodology that will allow the rapid insertion and positioning of medical implants through very small surgical incisions relative to the size of the implant.

It is an additional object of the present invention to provide surgical apparatus for rapidly inserting and positioning shape transformable surgical implants into a patient through a very small incision.

It is a still further object of the present invention to provide shape transformable surgical implants that can be inserted and positioned within a patient through a very small incision relative to the shape, size and volume of the implant.

It is a still further object of the present invention to provide shape transformable optical lenses that may be utilized for corrective or for pseudophakic purposes and which can be implanted into eyes in a rapid, small incision surgical technique.

SUMMARY OF THE INVENTION

These and other objects are achieved by the implants, methods, and apparatus of the present invention which can rapidly and simply insert and position shape transformable medical implants into a patient's body. In accordance with broad, functional aspects of the present invention the shape transformable medical implants are formed of elastomeric or gelatinous materials capable of substantial recoverable deformation in all dimensions. It was unexpectedly discovered by the present inventor that medical implants formed of these materials can be drawn into and ejected through very small diameter, elongate, generally tubular ejectors which require only very small surgical openings to provide access to the target site within the patient's body. Following implantation, the implants immediately reassume their pre-implant shapes and contours, allowing the implanting surgeon to immediately confirm proper placement and completion of the implantation procedure.

Unlike prior art implants intended for small incision surgical implantation, the implants of the present invention are capable of recoverable deformation in all dimensions. Thus, while the volume of the implant remains constant, the three-dimensional shape can be significantly altered into a very small diameter elongate form that, surprisingly, will readily and easily pass through a very small bore implantation ejector with minimal effort. Thus, broadly speaking, the method of the present invention simply involves loading the shape transformable implant into an ejector having a small diameter, elongate, generally tubular outlet, inserting and positioning the outlet into a target site within the patient's body and ejecting the implant through the elongate tubular outlet into the target site. If desired, the diameter of the elongate tubular outlet is sufficiently small to enable the outlet to function as a puncturing cannula analogous to a hypodermic needle capable of forming its own access pathway. Alternatively, a small surgical incision can be made utilizing conventional surgical techniques and the tubular outlet can be inserted therethrough.

The medical implant may be loaded into the ejector apparatus of the present invention by either aspirating or drawing the implant into the tubular outlet, or by positioning the implant within the ejector upstream of the tubular outlet and then forcing the implant through. In either event, the implant preferably is passed through the ejector outlet during the implantation procedure by pressurizing the ejector in a controlled manner. Precise pressure control enables the implanting surgeon to avoid inadvertent pressurization of the target site. Moreover, once the ejection process has been initiated to the point that the medical implant expands outwardly beyond the diameter of the tubular outlet, the internal recovery properties of the gelatinous material actually assist in pulling the implant through the ejector into the target site. As a result, only minimal pressure is required to eject the implant during the implantation procedure.

Alternatively, it was also surprisingly discovered that the shape transformable medical implants of the present invention may be placed within a detachable elongate tubular outlet having sufficient internal volume to retain the entire medical implant in its substantially distorted state. In this manner, the implant can be conveniently sterilized, stored, or transported within the detachable tubular outlet. For implantation, the implant-containing tubular outlet simply is attached to the pressurizable ejector prior to insertion and implantation.

The present invention is particularly well-suited for the implantation of optical lenses into the eye for corrective lens replacement (pseudophakic) purposes. The optical lenses can be formed from a wide variety of physiologically acceptable materials having an elongation at break of greater than 400% and an elastic modulus of less than 3,000 MPa. Exemplary materials for forming the medical implants of the present invention include hydrogels, silicone gels and elastomers, hydrocarbon gels and elastomers, peptide gels, and collagenous gels. When utilized as optical lenses, these gelatinous materials should be formulated to be optically transparent with a suitable final refractive index for light-focussing purposes. The optical lens implants may be configured as full-sized lenses, having diameters on the order of 8–13 mm or as conventionally-sized 5–7 mm optics which may include one or more radially extending haptic support structures. The cross-sectional shape of the optic lens may be any shape including plano-convex, biconvex, converging meniscus, diverging meniscus, plano-concave, and biconcave.

Other features and advantages of the present invention will become apparent to those skilled in the art from a consideration of the following detailed description taken in conjunction with the accompanying drawings which illustrate, by way of example, the principles of the present invention.

BRIEF DESCRIPTION OF THE DRAWINGS

FIG. 1 is a three-dimensional perspective view of an exemplary shape transformable implant illustrating the principles of the present invention and configured to function as an intraocular lens or ejectable lens implant;

FIG. 2 is a three-dimensional perspective view of an exemplary shape transformable implant analogous to that of FIG. 1 and provided with an alternative configuration;

FIG. 3 is a three-dimensional perspective view of an exemplary shape transformable implant analogous to that of FIG. 1 and provided with an additional alternative configuration;

FIG. 4 is a three-dimensional perspective view of an exemplary shape transformable implant analogous to that of FIG. 1 and provided with an alternative multipiece configuration;

FIG. 5a is a cross-sectional view of an exemplary shape transformable intraocular lens implant having a biconvex configuration;

FIG. 5b is a cross-sectional view of an exemplary shape transformable intraocular lens implant having a plano-convex configuration;

FIG. 5c is a cross-sectional view of an exemplary shape transformable intraocular lens implant having a plano-concave configuration;

FIG. 5d is a cross-sectional view of an exemplary shape transformable intraocular lens implant having a concavo-convex or meniscus configuration;

FIG. 6 is a fragmentary cross-sectional view of an exemplary multipiece ejector apparatus of the present invention shown provided with a removable loading funnel prior to implant loading;

FIG. 7 is a fragmentary cross-sectional view of the exemplary multipiece ejector apparatus of FIG. 6 illustrating the loading of a shape transformable implant;

FIG. 8 is a fragmentary cross-sectional view of the exemplary multipiece ejector apparatus of FIG. 6 following loading of the shape transformable implant and further illustrating an exemplary detachable implant containing tubular outlet;

FIG. 9 is a fragmentary cross-sectional view of an alternative exemplary ejector apparatus of the present invention shown prior to implant loading;

FIG. 10 is a fragmentary cross-sectional view of the alternative exemplary ejector apparatus of FIG. 9 shown following implant loading;

FIG. 14 is a diagrammatic fragmentary cross-sectional view of an eye and an alternative shape transformable implant containing ejector apparatus illustrating an alternative implantation procedure in accordance with the teachings of the present invention;

FIG. 15 is a diagrammatic fragmentary cross-sectional view of the eye and ejector apparatus of FIG. 14 during the implantation procedure; and FIG. 16 is a diagrammatic fragmentary cross-sectional view of the eye and ejector apparatus of FIG. 14 following the implantation procedure.

DETAILED DESCRIPTION OF EXEMPLARY EMBODIMENTS

Figure 11:
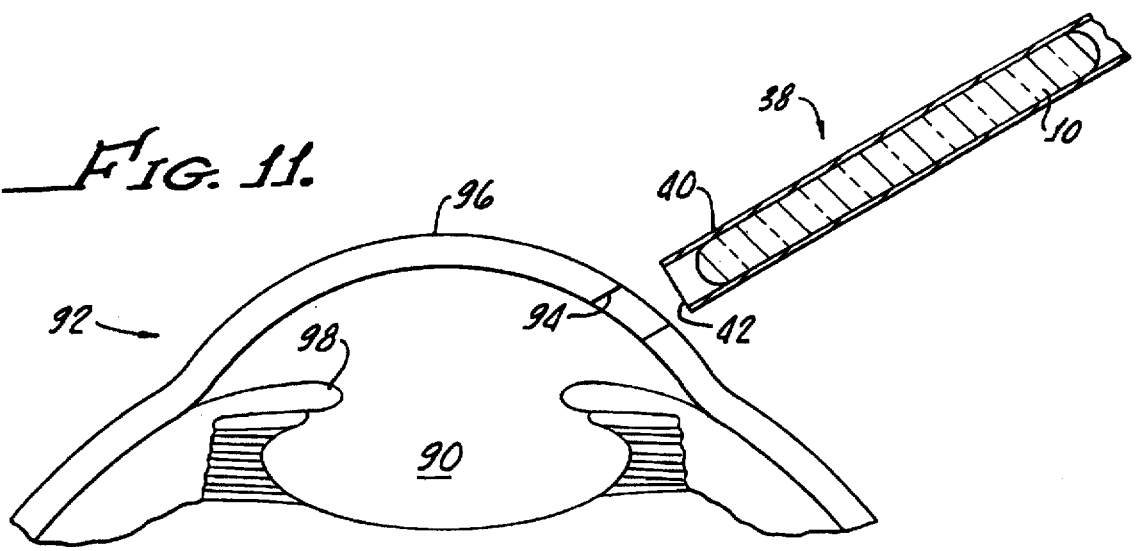
FIG. 11 is a diagrammatic fragmentary cross-sectional view of an eye and an exemplary shape transformable implant containing ejector apparatus illustrating an implantation procedure in accordance with the teachings of the present invention.

The following description is provided to enable any person skilled in the art to make and use the present invention and sets forth the best modes contemplated by the inventor of carrying out his invention. As those skilled in the art will appreciate, there are modifications, adaptation and alternatives within the scope and teaching of the present invention that will be readily apparent from the generic principles of the invention that have been specifically defined. The present invention provides methods and apparatus for the rapid and simple implantation of novel, shape transformable medical implants into a patient utilizing very small surgical access incisions.

Though many forms of shape transformable medical implants are contemplated as being within the scope of the present invention, for purposes of explanation and without limiting the scope of the present invention, the exemplary embodiments of the present invention will be discussed in the context of optical lens implants. Such lens implants are intended for use as corrective optics to assist the functioning of the natural lens or as pseudophakic or replacement optics where the natural lens has been damaged or removed from the eye. Optical lens implants are particularly well-suited for illustrating the principles of the present invention in that their beneficial light-focussing properties are directly determined by their physical shapes. Similarly, their placement, positioning, and retention within the patient's eye are also directly related to the functional shapes of the optical lens implants.

Referring more particularly to the drawings, FIG. 1 illustrates an exemplary shape transformable intraocular lens implant generally indicated by reference 10. Lens 10 is formed of a transparent material and is configured to function as a full-sized posterior chamber lens implant having a diameter on the order of 9 mm and a central thickness on the order of 4.5 mm. As will be discussed in detail below, the material forming lens 10 possesses a range of mechanical properties closer to those of a liquid rather than a solid. Nevertheless, in its non-stressed state, the material will retain its intended shape so that lens 10 can be designed and produced to function as a corrective or pseudophakic replacement lens having known, precisely controlled dioptric powers and closely controlled dimensions. However, in addition to the ability to manufacture lens 10 to exacting production tolerances, the material forming lens 10 is capable of substantial recoverable deformation in all dimensions so that lens 10 is shape transformable and can be implanted in accordance with the teachings of the present invention.

Similarly, FIG. 2 illustrates an alternative intraocular lens implant generally indicated by reference 12. Alternative intraocular lens 12 is also formed of a gelatinous or elastomeric material providing a rapidly recoverable, shape transformable capability. However, unlike the fully functional optic configuration of lens implant 10, alternative lens implant 12 is configured to include a generally centrally disposed light-focussing lens element 14 provided with a radially extending, generally planar, circular flange support haptic 16. In the embodiment shown, lens element 14 and support haptic 16 are formed of the same transparent gelatinous material. However, it is contemplated as being within the scope of the present invention to form support haptic 16 of a material having different properties from that of lens element 14. As those skilled in the art will appreciate, lens implant 12 is also configured to function as a posterior chamber pseudophakic implant. Thus, the overall diameter of lens implant 12 is also on the order of 9 to 13 mm while the diameter of lens element 14 is on the order of 5–7 mm. Following implantation, radially extending flange support haptic 16 will function to engage internal structures within the posterior chamber of the eye to position lens element 14 along the optical axis of the eye.

An additional alternative lens implant is illustrated in FIG. 3 and identified by reference 18. Like lens implant 12, lens implant 18 is configured to include a centrally disposed, light-focussing lens element 20 having a diameter on the order of 5–7 mm. Projecting from the circumferential periphery of lens element 20 is a plurality of generally planar blade haptics 22, 24, 26 and 28. These projecting blade haptic structures also function to support lens element 20 in position along the optical axis of the eye following implantation. In addition to reducing the overall volume and mass of lens 18 relative to lenses 10 and 12, the open configuration provided by blade haptics 22, 24, 26 and 28 is suitable for use within the anterior chamber of the eye as well as in the posterior chamber because the spaced apart blade haptics will not obstruct the trabecular meshwork about the periphery of the anterior chamber.

For ease of manufacture, blade haptics 22, 24, 26 and 28 may be formed of the same material as that forming lens element 20. Alternatively, as with lens implant 12, lens element 20 of lens implant 18 may be formed of an optically transparent, appropriately light refractive shape transformable material, while blade haptics 22, 24, 26 and 28 may be formed of a shape transformable material that is more suitable for maintaining the position of implant 18 in the eye. Thus, the haptics of these exemplary lenses of FIGS. 2 and 3 may be formed of materials having greater stiffness and resiliency than those of their associated lens elements. Moreover, because the haptics are not functioning in a light-focussing manner, they may be formed of colored or even opaque materials to assist the implanting surgeon in verifying their placement within the eye. It should also be noted that while four blade haptics are shown in this exemplary embodiment of lens 18, lens implants in accordance with the teachings of the present invention can be configured with alternative numbers of haptics, preferably two or more.

A multipiece alternative intraocular lens implant suitable for practicing the present invention is illustrated in FIG. 4 and generally indicated by reference 30. Multipiece lens implant 30 includes a central light-focussing lens element 32 formed of a transparent, relatively high refractive index shape transformable material such as that of lens implants 10, 12 and 18. Lens element 32 has a diameter on the order of 5–7 mm and a central thickness of 1–3 mm, like that of exemplary lens element 20 in implant 18. Loop haptics 34 and 36 extend from the periphery of lens element 32. As with conventional multipiece lenses, haptics 34 and 36, are formed as separate structural elements and are subsequently incorporated into the overall structure of lens implant 30. In order to function as effective support elements having sufficient structural rigidity to maintain lens element 32 in position along the optical axis of the eye following implantation, loop haptics 34 and 36 are preferably formed of materials such as polyamide, PTFE, or PVDF, or of other suitable materials through conventional techniques known in the art. These techniques include extrusion, etching, and stamping or die cutting the haptics prior to their being cast, glued or stapled into place in lens element 32. As those skilled in the art will also appreciate, the configuration of multipiece lens implant 30 is well-suited for use in either the anterior or posterior chamber of the eye. To assist in the implantation methodology of the present invention, it is preferred that loop haptics 34 and 36 be generally diametrically opposed as this facilitates their ejection and implantation through a very small surgical incision.

Though each of the alternative exemplary lens embodiments illustrated in FIGS. 1 through 4 are shown with biconvex lens elements, it is contemplated as being within the scope of the present invention to configure the light-focussing lens elements of the lens implants in any of a wide variety of optical lens configurations depending upon light focussing needs. Thus, as illustrated in FIGS. 5a through 5d, exemplary alternative cross-sectional lens shapes or configurations may include biconvex, as shown in FIG. 5a, plano-convex, as shown in FIG. 5b, plano-concave, as shown in FIG. 5c, and concavo-convex or meniscus, as shown in FIG. 5d. Other alternative cross-sectional lens configurations are also within the scope of the present invention, as dictated by the light-focussing needs of the individual patient. However, these exemplary lens cross-sections are more typical of those presently known in the art. Each has its own light-focussing properties and attendant manufacturing benefits or difficulties. For example, the plano-convex and plano-concave lens configurations of FIGS. 5b and 5c are the simplest to manufacture as it is necessary to produce only one curved optical surface on each lens. However, it should be noted that to achieve effective light focussing, these lens shapes generally require thicker optics to compensate for the refractive properties of the planar face. In contrast, the biconvex lens of FIG. 5a and the concavo-convex lens of FIG. 5d can be made thinner yet they require that the opposing curved lens surfaces of each lens have their respective optical centers aligned along the optical axes of each lens in order to avoid light distortion and aberration.

In the past, this alignment requirement has complicated the manufacture of such lenses due to the fact that it is difficult to machine such precisely shaped and aligned surfaces on the small lens structures. However, because the materials forming the lenses of the present invention are more suitable for casting and molding techniques, it is possible to manufacture a single precision mold that will consistently produce aligned optical lens surfaces. Thus, with the present invention, it is possible to produce a virtually limitless number and variety of precisely shaped lens configurations. Further, for multipiece lenses, such as those of implant 30 of FIG. 4, it is possible to cast the projecting haptics 34 and 36 into place within lens element 32 with minimal difficulty.

It should also be noted that there are additional functional advantages that may be associated with the biconcave lens configuration of FIG. 5a and the concavo-convex lens configuration of FIG. 5d. Because of the rapidly shape transformable properties of these implants, the symmetrical shape of FIG. 5a provides a lens that may "accommodate" within the posterior chamber of the eye to provide the implant patient with a variable focus ability like that of the natural lens. This is one of the ultimate objectives of the lens implantation art. Additionally, the projecting rear concave surface of the lens may function to stretch the posterior capsule following implantation to prevent distorting wrinkles and, possibly, to prevent subsequent opacification of the capsule. Alternatively, the meniscus configuration of FIG. 5d may also be distorted by the natural structures within the posterior chamber of the eye to provide a change in focal length and subsequent accommodation, while providing a space between the concave rear surface of the lens and the posterior capsule. This space may be preferred by some practitioners skilled in the art as it simplifies subsequent procedures such as a laser posterior capsulotomy should opacification of the posterior capsule occur following implantation surgery.

Regardless of the lens implant configuration or lens element cross-sectional shape chosen, the major portion of the implants of the present invention should be formed of elastomeric or gelatinous, highly extensible materials having elastic memories which provide shape transformable implants capable of substantial recoverable deformation in all dimensions. Exemplary materials suitable for practicing the present invention include hydrogels, silicone gels and elastomers, hydrocarbon gels, elastomers, polymers, oligomers, and oils, as well as gels and elastomers from natural sources, including peptides and collagens. As known in the art, gelatinous materials generally consist of polymeric elastomers incorporating low molecular weight plasticizers or lightly crosslinked, elastomeric networks.

Hydrophilic polymers, such as the hydrogels, are particularly suitable for practicing the present invention because water is the plasticizer accounting for the elasticity of these gelatinous materials. Additionally, extensive experience with hydrogel contact lenses has established the biocompatibility of these materials, making them excellent candidates for ejectable medical implants. Exemplary hydrogels suitable for practicing the present invention include polymers and copolymers of 2-hydroxyethyl methacrylate, vinylpyrrolidone, N-(2-hydroxyethyl) methacrylamide, and 2-3-dihydroxypropyl methacrylate. These materials can be compounded to incorporate sufficient cross-linking and water content for shape transformable resilient deformation, as desired.

Silicone gels and elastomers also provide ideal candidate materials for the ejectable shape transformable medical implants of the present invention. Like the hydrogels, silicone gels have an extensive history of biocompatible use. Moreover, the lightly crosslinked silicone gel network may be further polymerized, crosslinked or chemically bound within the material to enhance its biocompatibility and to prevent migration or leeching of the plasticizers.

The same is true with respect to the plasticizers incorporated into hydrocarbon polymers, oligomers, elastomers and oils. For example, triblock copolymers of poly(styrene-ethylene-butylene-styrene) including plasticizing oils, preferably chemically bound, in sufficient quantity to provide the appropriate properties, are suitable for practicing the present invention. Other suitable hydrocarbon polymers include polybutadiene, polyisoprene, polypropylene, polyethylene, polyvinylidene fluoride, polyvinyl chloride, polybutylene, polystyrene, polycyclopentene, and their copolymers and blends.

As noted above, the materials forming the implants of the present invention possess mechanical properties closer to those of liquids rather than those of solids. There is a wide spectrum of mechanical properties for materials ranging from solids to liquids. The following table is illustrative of these comparative property ranges.

TABLE 1

| Property | Water (Liquid) | Gelatinous Elastomer | Natural Rubber | Silicone Elastomer | PMMA (Solid) |
|---|---|---|---|---|---|
| Tensile strength (MPa) | 0 | 0.1–10 | 20 | 1.5–20 | 70 |
| Elastic modulus (MPa) | 0 | 0.001–0.1 | 1 | 100 | 3000 |
| Shear modulus (MPa) | 0 | 0.001–0.1 | 0.4 | 50 | 1700 |
| Ultimate elongation (%) | N/A | 400–3000 | 800 | 100–900 | 5 |
| Durometer Shore A | 0 | <1 | 20–80 | 5–80 | >100 |

Thus, exemplary shape transformable materials appropriate for practicing the present invention will have a tensile strength of less than 70 MPa, an elastic modulus of less than 3,000 MPa, a shear modulus of less than 1700 MPa, an elongation at break of greater than 100%, and a Durometer Shore A hardness of less than 100. Preferably, the materials will have an elastic modulus of less than 100 MPa, a shear modulus of less than 50 MPa, an elongation at break of greater than 400%, and a Durometer Shore A hardness of less than 20. An even more preferable range of shape transformable material properties appropriate for the present invention includes an elongation at break of greater than 900% and a Durometer Shore A hardness of less than 1.

However, it should be emphasized that these exemplary ranges of mechanical properties may be varied within the scope and teaching of the present invention in order to achieve additional desirable properties. For example, some materials such as hydrogels may require sufficient cross-linking to resist tearing such that their elastic modulus and shear modulus are within these exemplary ranges, whereas their elongation at break may be reduced. Similarly, achieving a sufficient refractive index for light-focussing purposes may alter these mechanical properties. Thus, it should be appreciated that it is a balance of these mechanical properties that is most suitable for practicing the present invention.

Further, for the light-focussing lens elements, it is preferred that the materials be compounded to exhibit a refractive index on the order of 1.4 or greater as this reduces the size and thickness of the lens element necessary to achieve the desired optical properties. It should also be noted that where strength and stability are required, it is possible to compound the materials to exhibit the appropriate degree of mechanical stiffness as long as they possess sufficient multidimensional shape transformable elasticity to allow for their implantation utilizing the methods of the present invention.

The implants themselves may be manufactured utilizing any suitable technique known in the art, such as casting, compression molding, injection molding, die cutting and the like. Additionally, it is contemplated as being within the scope of the present invention to coat the implants with a deformable skin that may be formed of a material having additional beneficial properties such as shape retention, biocompatibility, impermeability, and the like. Alternatively, an appropriately configured membrane may be filled with the shape transformable material to form the implant.

An exemplary shape transformable lens was prepared from silicone gel as follows. Commercially available silicone gel material was purchased from Hüls America, Inc. of Piscataway, N.J., and identified as Catalog No. PEG 015, supplied as Parts A and B. 5 grams of Part A were combined with 0.5 gram of Part B and mixed well in a beaker. The mixture was pre-cured at 110° C. for approximately fifteen minutes until the mixture became sufficiently viscous for transfer molding purposes. A transfer mold dimensioned to produce a full-sized intraocular lens, such as that illustrated in FIG. 1 having a diameter of 11 mm, a central cross-sectional thickness of 5 mm, and an edge thickness of 2 mm, was cleaned with a 1% sodium lauryl sulfate aqueous solution and the viscous pre-cured silicone material was transferred to the mold. Prior to closing the mold, the silicone material was degassed under vacuum for approximately ten minutes. The mold was closed, placed on a Carver press under 3,000 psi and cured at 120° C. for forty minutes. Following curing, the mold was allowed to cool to room temperature.

The same transfer mold and lens formation technique was utilized to form a silicone gel lens prepared from a mixture formed of equal parts of the PEG 015 silicone gel and soft silicone elastomer obtained from Hüls America, Inc. and identified as Catalog No. PELD 15.

With this understanding in mind, the method and implantation apparatus of the present invention can be understood as follows. FIGS. 6, 7, and 8 sequentially illustrate the loading of an exemplary shape transformable lens implant 10 into an ejector apparatus generally indicated by reference 38. Lens implant 10 is shown in cross-section to emphasize its largest cross-sectional dimension, a diameter of up to 13 mm. As discussed above, lens implant is formed of a material having substantial recoverable deformation in all dimensions and, because it is intended to function as an optical device in this exemplary embodiment, lens 10 is formed of an optically transparent material having a refractive index on the order of 1.4 or greater.

Ejector 38 includes an elongate, tubular member 40 formed of relatively thin wall tubing and provided with an outlet end 42. Slidably disposed in sealing engagement within tubular member 40 is piston 44. Piston 44 is attached to extending pushrod 46 provided with an enlarged plunger handle 48 and slidably mounted within plunger bore 50 of plunger housing 52. As shown in FIGS. 6 and 7, elongate tubular member 40 is detachably coupled within a receiving bore 54 provided in plunger housing 52. Preferably, for ease of manufacture, elongate tubular member 40 is provided with a circular cross-sectional shape having a relatively small diameter and a length sufficient to produce a total internal volume greater than the volume of shape transformable lens implant 10. For example, assuming lens implant 10 is a full-sized, fully functional optic, biconcave intraocular lens having a diameter of 10 mm and a total volume on the order of 250 mm$^3$, the volume of the cylindrically shaped internal bore of tubular member 40 will be greater than 250 mm$^3$, preferably on the order of 5% to 10% greater.

In the exemplary embodiment shown in FIGS. 6, 7 and 8, tubular member 40 functions as an elongate, generally tubular outlet of ejector apparatus 38. Accordingly, in order to provide an ejector apparatus capable of delivering a shape transformable implant through a minimal surgical incision on the order of 4.5 mm or less in length, the overall outer diameter of tubular member 40 is preferably on the order of 3.5 mm or less. Assuming that tubular member 40 is formed of a surgically compatible material such as stainless steel, polyamide, PVC, PTFE or the like, and allowing for a sufficient wall thickness to provide adequate strength, this leaves room for an internal diameter of approximately 3 mm or less. Thus, in the exemplary embodiment of ejector apparatus 38 shown, tubular member 40 will have a length of approximately 88 to 100 mm. The corresponding dimensions of piston 44 and pushrod 46 should be sufficient to allow ejector 38 to function in a manner analogous to a hypodermic syringe having a barrel defined by tubular member 40 that can be positively or negatively pressurized by advancing or retracting the plunger defined by piston 44, pushrod 46 and plunger handle 48.

A detachable converging loading funnel 56 is provided to facilitate the loading of shape transformable lens implant 10 into tubular member 40 of ejector apparatus 38. As shown most clearly in FIG. 8, detachable converging loading funnel 56 is provided with an enlarged implant receiving opening 58 and a conical bore 60 converging to a mating orifice 62. Preferably, mating orifice 62 has a generally circular cross-sectional configuration and a diameter substantially equal to that of the internal diameter of outlet end 42 on tubular member 40 when tubular member 40 is positioned within funnel receiving bore 64 as shown in FIGS. 6 and 7. At present, experimental work indicates that conical bore 60 should converge from implant receiving opening 58 to mating orifice 62 at the relatively shallow angle of approximately 15°. Further, loading funnel 56 should be of sufficient length to provide implant receiving opening 58 with a diameter ranging from approximately 4 mm to 15 mm.

In accordance with the teachings of the present invention, positioning shape transformable lens implant 10 in sealing engagement with implant receiving opening 58 of converging loading funnel 56 and withdrawing the plunger defined by piston 44, pushrod 46 and plunger handle 48 from apparatus 38 in the direction of arrow 66 precisely reduces the pressure within tubular member 40 drawing shape transformable lens implant 10 into ejector apparatus 38. The substantial recoverable deformation property of shape transformable lens implant 10 allows it to assume a rod-like shape within tubular member 40 as shown in FIG. 8. Following this loading procedure, converging loading funnel 56 is removed from outlet end 42 of elongate tubular member 40 to define an ejector having a small diameter, elongate, generally tubular outlet with a gelatinous lens implant loaded therein.

It should be noted that while the exemplary embodiment illustrated in FIGS. 6, 7 and 8 is provided with a detachable elongate tubular outlet formed by tubular member 40, this feature is not essential to the practice of the present invention. However, detachable tubular member 40 containing lens 10 provides a number of desirable benefits. For example, the lens-containing tubular member can be conveniently sterilized, stored, or transported. Alternatively, if desired, the implanting surgeon can load a sterilized implant directly into the tubular member at the site of operation.

To facilitate the loading of the implant into the tubular outlet, it may be desirable to utilize a surgically acceptable lubricant or viscoelastic material, such as sodium hyaluronate. In addition to lubricating the surfaces of the gelatinous implant and the internal surfaces of the ejector apparatus, the viscoelastic material also aids in sealing the lens implant into the implant receiving opening 58 of loading funnel 56 so that the implant may be easily drawn into tubular member 40. Contrary to anticipation, it was surprisingly discovered that a rapid and strong negative pressure is more effective at loading the implant into tubular member 40 than is a slow, smooth negative pressure.

For example, the previously discussed full-sized exemplary silicone intraocular lenses having an 11 mm and a 5 mm central thickness were shape transformed into small diameter elongate rods having an overall length of approximately 23 mm and a diameter of 4 mm by coating the lenses with sodium hyaluronate and sucking each lens into the apparatus of FIG. 6. Following ejection from the tubular outlet of the apparatus, each lens assumed its pre-transformation shape.

Additionally, while the conical bore 60 of converging loading funnel 56 is illustrated with a generally circular cross-sectional shape, it is also contemplated as being within the scope of the present invention to provide bore 60 with an elliptical cross-sectional shape, having its long axis aligned with the larger dimension or diameter of shape transformable lens implant 10. In this manner, it may be possible to control the planar orientation of lens implant 10 as it is drawn into tubular member 40. This will allow the implanting surgeon to control the planar orientation of the implant during the ejection and implantation procedure. This alignment orientation plane aspect of converging loading funnel 56 is less important with symmetrical implants, such as that illustrated in FIG. 5a. However, it may provide significant implantation advantages with asymmetrical implants, such as those illustrated in FIGS. 5b, 5c and 5d, as the alignment orientation plane will enable the implanting surgeon to control which face of the implant is positioned where within the eye.

Referring now to FIGS. 9 and 10, an alternative ejector apparatus 68 is provided with an internal converging loading funnel 70 upstream of and in fluid conducting communication with a small diameter, elongate, generally tubular outlet 72 having an outlet end 74. At the implant-receiving end 76 of internal converging loading funnel 70 is a pressurizable lens-receiving chamber 78. Though the exemplary embodiment of alternative ejector apparatus 68 shown is of an integral or one-piece construction, it should be emphasized that tubular outlet 72 and lens-receiving chamber 78 may be detachable elements, if desired.

In order to load a shape transformable implant, such as lens implant 10, into alternative ejector apparatus 68, implant 10 is simply positioned within lens-receiving chamber 78 through large diameter opening 80, followed by insertion of a pressure controlling plunger defined by piston 82 mounted upon pushrod 84. As with piston 44 of ejector apparatus 38 of FIGS. 6, 7 and 8, piston 82 is configured to sealingly engage the internal surfaces of pressurizable lens-receiving chamber 78. Accordingly, piston 82 is provided with the appropriate cross-sectional shape and dimensions to provide an effective sliding seal analogous to that of a hypodermic syringe. However, with alternative ejector apparatus 68, the dimensions of pressurizable lens-receiving chamber 78 may be closer to that of the undeformed implant as the internal converging loading funnel 70 is located at the opposite end of pressurizable lens-receiving chamber 78. Similarly, while it is preferable that the diameter of elongate tubular outlet 72 be as small as possible, the length of tubular outlet 72 is more appropriately determined by the needs of the implanting surgeon, rather than by the internal volume constraints of tubular member 40 which necessarily must contain the entire implant 10. As a result, elongate tubular outlet 72 may be considerably shorter than tubular member 40 of ejector apparatus 38.

In FIG. 10, shape transformable implant 10 is shown positioned within pressurizable lens-receiving chamber 78 and surrounded by viscoelastic lubricant 86. Viscoelastic 86 functions to lubricate shape transformable implant 10 and to provide a uniform hydraulic pressure within lens-receiving chamber 78 so that the pressure within chamber 78 can be precisely controlled through the movement of piston 82. Advancing piston 82 in the direction of arrow 88 positions implant 10 within internal converging loading funnel 70 prior to ejection through tubular outlet 72. In this manner, ejector apparatus 68 is loaded as the first or preliminary step to implantation of implant 10.

In a broad aspect, the implantation methodology of the present invention comprises the basic steps of inserting and positioning the small diameter, elongate, generally tubular outlet of an implant loaded ejector into a surgical target site and ejecting the shape transformable implant through the tubular outlet. An example of this procedural methodology is illustrated sequentially in FIGS. 11, 12 and 13. Though illustrated in the context of an intraocular lens insertion procedure, those skilled in the art will appreciate that the implantation methodology of the present invention is widely suitable for inserting and positioning a variety of implants within various target sites.

Figure 12:
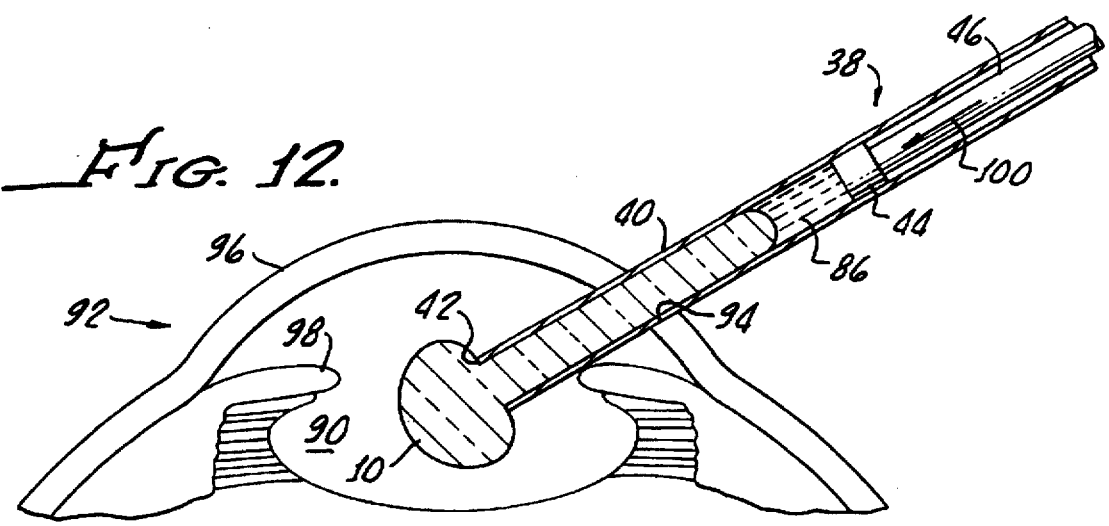
FIG. 12 is a diagrammatic fragmentary cross-sectional view of the eye and ejector apparatus of FIG. 11 during the implantation procedure.
Figure 13:
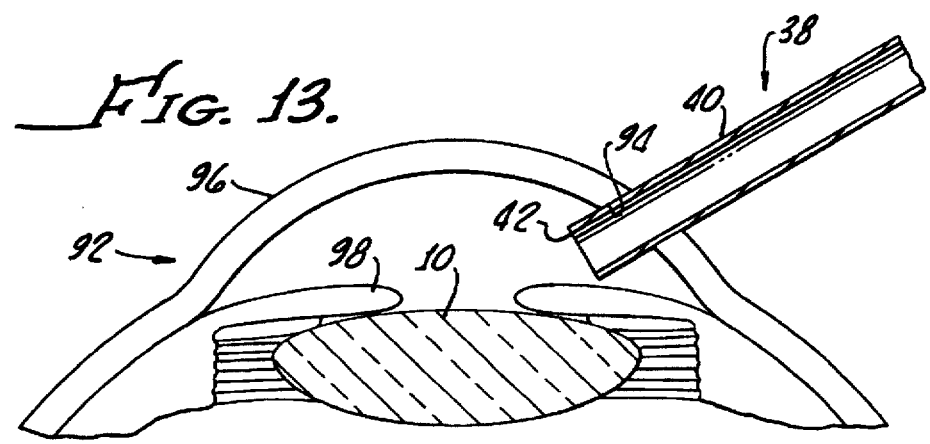
FIG. 13 is a diagrammatic fragmentary cross-sectional view of the eye and ejector apparatus of FIG. 11 following implantation.

In the exemplary embodiment shown in FIGS. 11, 12 and 13, the target site is the posterior chamber 90 of an eye, itself generally indicated by reference 92. A small scale surgical incision 94 is made in cornea 96, preferably at the corneal scleral junction at the peripheral edge of cornea 96 to provide access to the interior of eye 92. An elongate tubular member 40 loaded with a shape transformable, gelatinous intraocular lens implant 10 is advanced through surgical incision 92 so that the outlet end 42 of tubular member 40 is positioned within the vicinity of posterior chamber 90 behind pupillary iris 98. With particular reference to FIG. 12, once tubular member 40 has been inserted and positioned into the target site within eye 92, piston 44 of ejector apparatus 38 is advanced in the direction of arrow 100 by the movement of pushrod 46 to increase the pressure within tubular member 40. Viscoelastic lubricant 86 is provided within tubular member 40 to facilitate the precise control of this pressurization. As a result, shape transformable lens implant 10 is advanced through tubular member 40 and out through outlet end 42.

Interestingly, it also was surprisingly discovered that once a sufficient portion of the shape transformable implant has been ejected through outlet end 42 of the ejector, the pressure provided by piston 44 can be reduced and the implant will continue to extrude or pass through the outlet end of the ejector. Without wishing to be bound to this theory, it is believed that the internal recoverable elastic properties of the shape transformable material forming the implant function to draw the remaining portions of the implant out of the tubular member. A very small amount of pressure may be utilized to assist the advancement and ejection of the implant into the target site. Accordingly, it is preferred that the ejector apparatus be provided with some means for precisely controlling the pressure within the lens-containing or lens-receiving chamber. In these exemplary embodiments, the pressure controlling means is a manually advanced plunger, as defined. However, it is contemplated as being within the scope of the present invention to utilize alternative forms of precise pressure control, such as advancing screws or electromechanical or electrohydraulic devices, as known in the art.

As shown in FIG. 13, implant 10 immediately recovers its initial pre-implantation shape and configuration as soon as it is ejected through tubular outlet 40. This allows the implanting surgeon to withdraw the ejector apparatus 38 from eye 92 and to verify the proper placement and positioning of implant 10. If necessary, implant 10 can be manipulated once in place using conventional surgical techniques and tools. However, unlike conventional prior art intraocular lenses, which rely upon notches and holes for the placement of manipulating instruments, the gelatinous implants of the present invention can be reliably engaged and manipulated with existing surgical probes and the like simply by pushing the instrument to deform the lens into engagement. Removal of the instrument allows the implant to immediately resume its intended shape and configuration.

Those skilled in the art will recognize that implant 10 illustrated in FIG. 13 is a biconvex, posterior chamber implant that essentially completely fills the posterior chamber of eye 92 in order to replace a missing or removed natural lens. An alternative implantation procedure is illustrated in FIGS. 14, 15 and 16 where the natural lens of the eye remains intact. In this alternative procedure, a normal eye 92 including natural lens 102 is provided with an anterior chamber lens implant functioning as an injectable or implantable corrective contact lens in the following manner. First, an ejector apparatus 68, analogous to that discussed with respect to FIGS. 9 and 10, is provided with a self-piercing, hypodermic needle-like outlet end 104 which enables the small diameter, elongate, generally tubular outlet 72 to be directly inserted through cornea 96 into the anterior chamber 106 of eye 92. Gelatinous, shape transformable lens implant 18, as discussed with respect to FIG. 3, having been previously loaded into ejector 68, is advanced through tubular outlet 72 by ejecting implant 18 through outlet end 104 and into anterior chamber 106 in front of pupillary iris 98. Once free of the confines of tubular outlet 72, shape transformable implant 18 immediately recovers its original configuration wherein projecting blade haptics 22 and 26 position lens element 20 in front of pupillary iris 98 to function as a corrective lens in conjunction with natural lens 102. At essentially the same moment in time, tubular outlet 72 is removed through cornea 96 while the implanting surgeon verifies the positioning and orientation of implant 18 prior to closing puncture incision 108.

Those skilled in the art Will understand that the preceding exemplary embodiments of the present invention provide the foundation for numerous alternatives and modifications thereto. These other modifications are also within the scope of the present invention. Thus, by way of example, but not of limitation, the shape transformable implants of the present invention may be configured to function as cosmetic implants for reconstructive or augmentation purposes. Such implants would include artificial chins, cheekbones, noses, ears and other body parts including breasts and penile implants. Similarly, alternative ejector apparatus may be configured to function with such implants utilizing the principles and teachings of the present invention. Such alternative ejector apparatus would be configured to accommodate the overall volume and minimum distorted dimensions achievable with the gelatinous implants. In this manner, a wide variety of implants may be surgically inserted and positioned through minimal, relatively atraumatic surgical incisions. Accordingly, the present invention is not limited to that precisely as shown and described in the present invention.

What is claimed is:

1. A method for performing lens replacement in an eye, the method comprising the steps of:

providing a shape-transformable optical lens capable of substantial recoverable deformation in all dimensions and formed of an optically transparent material having a tensile strength of less than about 70 MPa, an elastic modulus of less than 3,000 MPa, an elongation at break of greater than 100%, and a Durometer Shore A hardness of less than about 100;

loading said shape-transformable lens into a lens ejector having a small-diameter, elongate, generally tubular outlet configured to receive said shape-transformable optical lens in sliding sealing engagement;

inserting said small-diameter, elongate, generally tubular outlet into the eye;

positioning said small-diameter, elongate, generally tubular outlet at a target site within the eye; and ejecting said shape-transformable optical lens through said small-diameter, elongate, generally tubular outlet at the target site within the eye.

2. The method of claim 1 further comprising after said ejecting step the stop of:

positioning said shape-transformable optical lens at the target site within the eye.

3. The method of claim 1 wherein said inserting step further comprises the additional step of:

surgically forming an incision in the eye; and inserting said small-diameter, elongate, generally tubular outlet through said incision into the eye.

4. The method of claim 3 wherein said surgically forming step comprises the step of:

surgically forming an incision of less than about 4.5 mm in length in the eye.

5. The method of claim 4 wherein said providing step comprises the step of:

providing a shape-transformable optical lens capable of substantial recoverable deformation in all dimensions and having an overall diameter in the range of about 5 mm to 13 mm.

6. The method of claim 5 wherein said loading step comprises the step of:

loading said shape-transformable optical lens into a lens ejector having an elongate, generally tubular outlet configured to receive said shape-transformable optical lens in sliding sealing engagement and having a length of less than about 100 mm and an internal diameter of about 3 mm.

7. The method of claim 1 wherein said optical lens is loaded into said ejector through the additional steps of:

mounting a converging loading funnel dimensioned to receive said optical lens onto said small diameter, elongate, generally tubular outlet;

placing said optical lens into said converging loading funnel;

drawing said optical lens through said converging loading funnel and into said small diameter, elongate, generally tubular outlet; and removing said converging loading funnel from said small diameter, elongate, generally tubular outlet.

8. The method of claim 7 wherein said small diameter, elongate, generally tubular outlet containing said optical lens is detachable from said ejector.

9. The method of claim 7 wherein said converging loading funnel is provided with a generally elliptical cross-sectional area defining an alignment orientation plane for maintaining a specific orientation of said optical lens within said small diameter, elongate, generally tubular outlet.

10. The method of claim 1 wherein said optical lens is loaded into said ejector through the additional steps of:

providing a converging loading funnel within said ejector upstream of and in communication with said small diameter, elongate, generally tubular outlet; and placing said optical lens into said converging loading funnel prior to ejecting said optical lens through said outlet of said small diameter, elongate, generally tubular outlet.

11. The method of claim 1 further comprising the additional step of lubricating said optical lens prior to ejecting said optical lens through said outlet of said small diameter, elongate, generally tubular outlet.

12. The method of claim 11 wherein said optical lens is lubricated through the additional step of coating said optical lens with a viscoelastic material.

13. The method of claim 1 wherein said optical lens is substantially deformed when received in sad small-diameter, elongate, generally tubular outlet.

14. A method of implanting an optical lens into an eye, the method comprising the steps of:

providing a shape-transformable optical lens capable of substantial recoverable deformation in all dimensions and formed of an optically transparent material having a tensile strength of less than about 70 MPa, an elastic modulus of less than 3,000 MPa, an elongation at break of greater than 100%, and a Durameter Shore A hardness of less than about 100;

loading said shape-transformable optical lens into a lens ejector having a small-diameter, elongate, generally tubular outlet configured to receive said shape-transformable optical lens in sliding sealing engagement;

inserting said small-diameter, elongate, generally tubular outlet into the eye;

positioning said small-diameter, elongate, generally tubular outlet at a target site within the eye; and ejecting said shape-transformable optical lens through said small-diameter, elongate, generally tubular outlet at the target site within the eye.

15. The method of claim 14 further comprising after said ejecting step the step of:

positioning said shape-transformable optical lens at the target site within the eye.

16. The method of claim 14 wherein said inserting step further comprises the additional step of:

surgically forming an incision in the eye; and inserting said small-diameter, elongate, generally tubular outlet through said incision into the eye.

17. The method of claim 16 wherein said surgically forming step comprises the step of:

surgically forming an incision of less than about 4.5 mm in length in the eye.

18. The method of claim 17 wherein said providing step comprises the step of:

providing a shape-transformable optical lens capable of substantial recoverable deformation in all dimensions and having an overall diameter in the range of about 8 mm to 13 mm.

19. The method of claim 18 wherein said loading step comprises the step of:

loading said shape-transformable optical lens into a lens ejector having an elongate, generally tubular outlet configured to receive said shape-transformable optical lens in sliding sealing engagement and having a length of less than about 100 mm and an into real diameter of about 3 mm.

20. The method of claim 14 wherein said optical lens is substantially deformed when received in said small-diameter, elongate, generally tubular outlet.

21. The method of claim 14 wherein said optical lens is loaded into said ejector through the additional steps of:

mounting a converging loading funnel dimensioned to receive said optical lens onto said small diameter, elongate, generally tubular outlet;

placing said optical lens into said converging loading funnel;

drawing said optical lens through said converging loading funnel and into said small diameter, elongate, generally tubular outlet; and removing said converging loading funnel from said small diameter, elongate, generally tubular outlet.

22. The method of claim 21 wherein said small diameter, elongate, generally tubular outlet containing said optical lens is detachable from said ejector.

23. The method of claim 21 wherein said converging loading funnel is provided with a generally elliptical cross-sectional area defining an alignment orientation plane for maintaining a specific orientation of said optical lens within said small diameter, elongate, generally tubular outlet.

24. The method of claim 14 wherein sad optical lens is loaded into said ejector through the additional steps of:

providing a converging loading funnel within said ejector upstream of and in communication with said small diameter, elongate, generally tubular outlet; and placing said optical lens into said converging loading funnel prior to ejecting said optical lens through said outlet of said small diameter, elongate, generally tubular outlet.

25. The method of claim 14 further comprising the additional step of lubricating said optical lens prior to ejecting said optical lens through said outlet of said small diameter, elongate, generally tubular outlet.

26. The method of claim 25 where, in said optical lens is lubricated through the additional step of coating said optical lens with a viscoelastic material.

* * * * *

UNITED STATES PATENT AND TRADEMARK OFFICE
CERTIFICATE OF CORRECTION

PATENT NO. : 5,702,441
DATED : December 30, 1997
INVENTOR(S) : Stephen Q. Zhou

It is certified that error appears in the above-indentified patent and that said Letters Patent is hereby corrected as shown below:

Column 15, line 37, between the words "transformable" and "lens" insert the word --optical--.

Column 15, line 49, delete the term "stop" between the words "the" and "of" and insert the word --step--.

Column 15, line 66, delete the numeral "5" at the end of the line and insert --8--.

Column 16, line 47, delete the term "sad" and insert the term --said--.

Column 17, line 30, delete the terms "into real" and insert the term --internal--.

Column 18, line 19, delete the term "sad" and insert the term --said--.

Column 18, line 32, delete "where, in" and insert --wherein--.

Signed and Sealed this

Fifth Day of May, 1998

*Attest:*

*Attesting Officer*

BRUCE LEHMAN
*Commissioner of Patents and Trademarks*